US00RE38984E

(19) United States
(12) Reissued Patent
Abruzzo et al.

(10) Patent Number: US RE38,984 E
(45) Date of Reissued Patent: Feb. 14, 2006

(54) ANTIFUNGAL COMBINATION THERAPY

(75) Inventors: George K. Abruzzo, Clark, NJ (US); Kenneth F. Bartizal, Hampton, NJ (US); Amy M. Flattery Feighner, Holmdel, NJ (US)

(73) Assignee: Merck & Co., Inc., Rahway, NJ (US)

(21) Appl. No.: 10/325,137

(22) PCT Filed: Sep. 9, 1997

(86) PCT No.: PCT/US97/15987

§ 371 (c)(1),
(2), (4) Date: Feb. 24, 1999

(87) PCT Pub. No.: WO98/10782

PCT Pub. Date: Mar. 19, 1998

Related U.S. Patent Documents

Reissue of:
(64) Patent No.: 6,069,126
Issued: May 30, 2000
Appl. No.: 09/242,831
Filed: Feb. 24, 1999

U.S. Applications:
(60) Provisional application No. 60/026,327, filed on Sep. 12, 1996.

(51) Int. Cl.
*A61K 38/00* (2006.01)
*A61K 31/70* (2006.01)
*A61K 31/45* (2006.01)

(52) U.S. Cl. ..... 514/11; 514/31; 514/394; 514/395

(58) Field of Classification Search ..... 514/11, 514/31, 394, 395
See application file for complete search history.

(56) References Cited

U.S. PATENT DOCUMENTS 5,030,619 A * 7/1991 Hector
5,348,970 A * 9/1994 Schwartz et al.
5,378,804 A * 1/1995 Balkovec et al.
5,514,650 A * 5/1996 Balkovec et al.
5,552,521 A * 9/1996 Belyk et al. ..... 530/317
5,627,153 A * 5/1997 Little, II et al.
5,741,775 A * 4/1998 Balkovec et al.

FOREIGN PATENT DOCUMENTS

HU 211 890 A9 12/1995
WO WO 94/21677 9/1994
WO WO 94 21677 * 9/1994
WO WO 98/10782 3/1998
WO 98/10782 * 3/1998

OTHER PUBLICATIONS

Franzot et al., Pneumocandin L–743,872 enhances the activities of amphotericin B and Fluconazole against Cryptococcus neoformans in vitro, Antimicrob. Agents Chemother., (1997), 41(2), 331–336 (abs.).*

ICAAC Abstract No. 821, entitled Pneumocandin L–7543–872 enhances the activity of Amphotericin B and Fluconazole against Cryprococcus neoformans in vitro by S. P. Franzot, et al.*

Antimicrobial Agents & Chemotherapy, pp. 1077–1081 (May 1995), by G. Abruzzo, et al.*

Antimicrobial Agents & Chemotherapy, pp. 1070–1076 (May 1995), by K. Barizal, et al.*

Antimicrobial Agents & Chemotherapy, vol. 41, No. 2, pp. 331–336 (1997), by S. Franzot, et al.*

Antimicrobial Agents & Chemotherapy, vol. 41, No. 10, pp. 2310–2311 (1997), by D. Law, et al.*

Antimicrobial Agents & Chemotherapy, vol. 42, No. 2, pp. 313–318 (1998), by J. Fung–Tomc, et al.*

Abstracts of the 36th ICAAC, Sep. 15–18, 1996, Tuesday, Session 83, p. 132.*

Abstracts of the 37th ICAAC, Sep. 28–Oct. 1, 1997, pp. 162–163.*

Abruzzo, et al., Antimicrobial Agents & Chemotherapy (May 1995), pp. 1077–1081.

Franzot, et al. ICAAC Abstract No. 821, entitled "Pneumocandin L–743,872 enhances the activity of Amphotericin B and Fluconazole against *Cryptococcus neoformans* in vitro".

Fung–Tomc, J., et al. Antimicrobial Agents & Chemotherapy, vol. 42, No. 2, pp. 313–318, 1998.

Law, D., et al. Antimicrobial Agents & Chemotherapy, vol. 41, No. 10, pp. 2310–2311, 1997.

Abstracts of the 36th ICAAC, Sep. 18–Oct. 1, 1997, pp. 162–163.

* cited by examiner

*Primary Examiner*—Kevin E. Weddington
(74) *Attorney, Agent, or Firm*—Richard S. Parr; Mark R. Daniel; Valerie J. Camara

(57) ABSTRACT

There is described antifungal combination therapy comprising the use of known antifungal agents such as the azoles or polyenes in combination with a pneumocandin derivative antifungal agent. More particularly, the invention relates to antifungal combination therapy comprising the use of azoles such as fluconazole, voriconazole, itraconazole, ketoconazole, miconazole, ER 30346, SCH 56592; polyenes such as amphotericin B, nystatin or liposomal and lipid forms thereof such as Abelcet, AmBisome and Amphocil; purine or pyrimidine nucleotide inhibitors such as flucytosine; or polyoxins such as nikkomycins, in particular nikkomycin Z or other chitin inhibitors, elongation factor inhibitors such as sordarin and analogs thereof, mannan inhibitors such as predamycin, bactericidal/permeability-inducing (BPI) protein products such as XMP.97 or XMP.127 or complex carbohydrate antifungal agents such as CAN-296 in combination with a pneumocandin derivative as described herein.

12 Claims, No Drawings

ANTIFUNGAL COMBINATION THERAPY

Matter enclosed in heavy brackets [ ] appears in the original patent but forms no part of this reissue specification; matter printed in italics indicates the additions made by reissue.

"This application claims the benefit of U.S. Provisional Application No. 60/026,327, filed Sept. 12, 1996."

FIELD OF THE INVENTION

The present invention relates to antifungal combination therapy comprising the use of known antifungal agents such as the azoles or polyenes in combination with a pneumocandin derivative antifungal agent. More particularly, the invention relates to antifungal combination therapy comprising the use of azoles such as fluconazole (hereinafter referred to as FCZ), voriconazole, itraconazole, ketoconazole, miconazole, ER 30346, SCH 56592; polyenes such as amphotericin B (hereinafter referred to as AmB), nystatin or liposomal and lipid forms thereof such as Abelcet, AmBisome and Amphocil; purine or pyrimidine nucleotide inhibitors such as flucytosine; or polyoxins such as nikkomycins, in particular nikkomycin Z or other chitin inhibitors, elongation factor inhibitors such as sordarin and analogs thereof, mannan inhibitors such as predamycin, bactericidal/permeability-inducing (BPI) protein products such as XMP.97 or XMP.127 or complex carbohydrate antifungal agents such as CAN-296 in combination with a pneumocandin derivative of the structure (I)

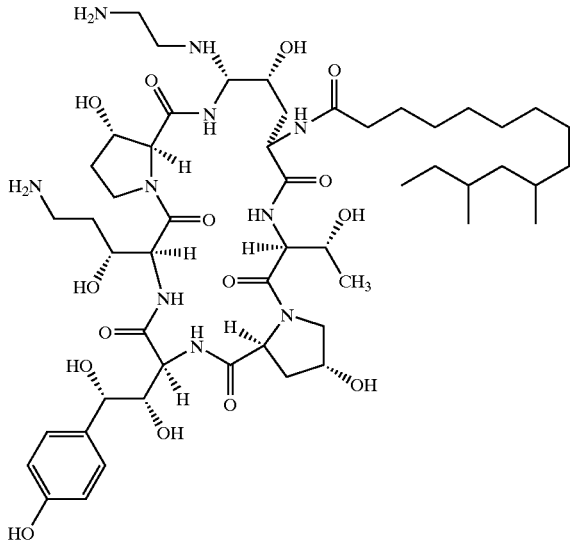

or a pharmaceutically acceptable salt or other pharmaceutically acceptable formulation thereof.

These combination therapies have been shown to be useful against such opportunistic pathogens as Cryptococcus spp., Candida spp., Aspergillus spp., Histoplasma spp., Coccidioides spp., Paracoccidioides spp. Blastomyces spp., Fusarium spp., Sporothrix spp., Trichosporon spp., Rhizopus spp., Pseudallescheria spp., dermatophytes, Paeciliomyces spp., Alternaria spp., Curvularia spp., Exophiala spp., Wangiella spp., Penicillium spp., Saccharomyces spp., Dematiaceous fungi and Pneumocystis carinii.

BACKGROUND OF THE INVENTION

There is an increasing need for agents which are effective against opportunistic mycotic infections by such agents as Cryptococcus spp., Candida spp., Aspergillus spp., Histoplasma spp., Coccidioides spp., Paracoccidioides spp. Blastomyces spp., Fusarium spp., Sporothrix spp., Trichosporon spp., Rhizopus spp., Pseudallescheria spp., dermatophytes, Paeciliomyces spp., Alternaria spp., Curvularia spp., Exophiala spp., Wangiella spp., Penicillium spp., Saccharomyces spp., Dematiaceous fungi and Pneumocystis carinii. The present treatments, i.e., polyenes, such as amphotericin B, cause severe side effects and azoles, such as fluconazole, are only fungistatic. The pneumocandins, which are related to the echinocandins, are cyclic hexapeptides which inhibit cell wall 1,3β-D-glucan synthesis. The pneumocandins have shown potent in vivo activity against Candida spp., Pneumocystis carinii, Aspergillus spp., as well as the other fungal pathogens listed above. However, the pneumocandins, by themselves, have weak activity against Cryptococcus spp.

Combination therapy with antifungal drugs may provide additional options for treating Cryptococcus and other fungal pathogens.

Previous studies have evaluated the efficacy of other pneumocandin derivatives against Cryptococcus neoformans in combination with amphotericin B and fluconazole (Abruzzo et al., Antimicrob. Agents Chemo. 1995, 39:1077–1081 and Bartizal et al., Antimicrob. Agents Chemo. 1995, 39:1070–1076). However, none of these studies have demonstrated the results found using Compound I as the pneumocandin derivative.

DETAILED DESCRIPTION OF THE INVENTION

The present invention relates to antifungal combination therapy comprising the use of known antifungal agents such as the azoles or polyenes in combination with a pneumocandin derivative antifungal agent. More particularly, the invention relates to antifungal combination therapy comprising the use of azoles such as fluconazole, voriconazole, itraconazole, ketoconazole, miconazole, ER 30346, SCH 56592; polyenes such as amphotericin B, nystatin or liposomal and lipid forms thereof such as Abelcet, AmBisome and Amphocil; purine or pyrimidine nucleotide inhibitors such as flucytosine; or polyoxins such as nikkomycins, in particular nikkomycin Z or other chitin inhibitors, elongation factor inhibitors such as sordarin and analogs thereof, mannan inhibitors such as predamycin , bactericidal/permeability-inducing (BPI) protein products such as XMP.97 or XMP.127 or complex carbohydrate antifungal agents such as CAN-296 in combination with a compound of the structure (I)

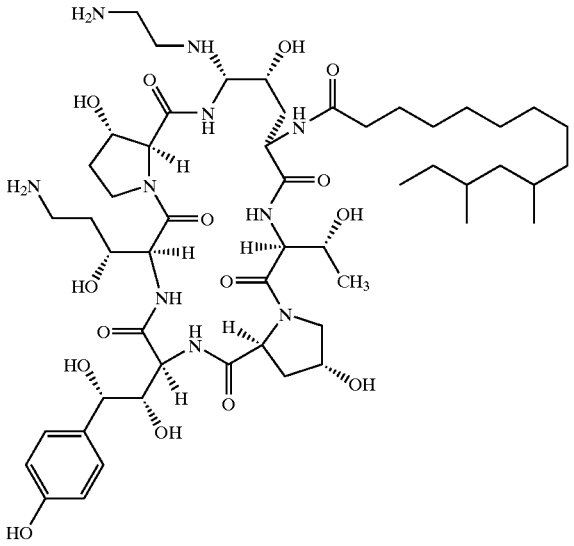

or a pharmaceutically acceptable salt or other pharmaceutically acceptable formulation thereof.

In particular, this combination therapy has been shown to be useful against such opportunistic pathogens as Cryptococcus spp., Candida spp., Aspergillus spp., Histoplasma spp., Coccidioides spp., Paracoccidioides spp. Blastomyces spp., Fusarium spp., Sporothrix spp., Trichosporon spp., Rhizopus spp., Pseudallescheria spp., dermatophytes, Paeciliomyces spp., Alternaria spp., Curvularia spp., Exophiala spp., Wangiella spp., Penicillium spp., Saccharomyces spp., Dematiaceous fungi and Pneumocystis carinii.

Compound I is disclosed in U.S. Pat. No. 5,378,804. Its preparation is described in that patent along with U.S. Pat. No. 5,552,521.

It is contemplated that other pneumocandin derivatives such as those disclosed in U.S. Pat. No. 5,516,756 and in copending applications 07/936,558, 07/936,561, 09/058,657, 09/055,996, 08/378,687 and 60/006,505 would be useful in the combination therapy.

The azole, polyene or other antifungal agent may be administered orally or parenterally. Compound I is preferably administered parenterally, but is not limited to that route and may also be administered by other routes such as oral, intramuscular or subcutaneous.

As shown below, the combination therapy results in enhanced effects using sub-inhibitory concentrations of all agents. These effects can be demonstrated in vitro and in vivo using clinical and environmental strains of C. neoformans, C. albicans and A. fumigatus.

The invention is further described in connection with the following non-limiting examples.

EXAMPLES

It has been found that combination therapy of Compound I with AmB and FCZ against C. neoformans results in enhanced activity against strains of C. neoformans in vitro. It has also been found that combination therapy of Compound I with AmB against C. albicans and A. fumigatus results in enhanced activity in vitro. This has been shown using a broth microdilution technique which is the standard method for antifungal susceptibility testing proposed by the NCCLS (protocol M27-T). Sub-inhibitory concentrations of Compound I in combination with sub-inhibitory concentrations of AmB and sub-inhibitory concentrations of FCZ were employed. The minimal inhibitory concentrations (MICS) for AmB and Compound I were defined as the lowest drug concentration at which there was an absence of growth. FCZ MIC was defined as the lowest drug concentration which resulted in a visual turbidity less than or equal to 80% inhibition compared with that produced by the control without antifungal agent.

Results of antifungal susceptibility testing show that colony forming units (CFUs) were markedly reduced when amphotericin B at certain concentrations (0.0075, 0.015 and 0.03 $\mu$g/ml) was combined with Compound I at certain concentrations (4, 8 and 16 $\mu$g/ml). Additionally, the administration of Compound I significantly enhanced the activity of fluconazole by reducing CFU numbers at certain concentrations (0.25, 0.50 and 1.0 $\mu$g/ml).

Additional drug combination testing in vitro was performed to evaluate combinations of Compound I with AmB and FCZ against clinical isolates. There was no antagonism evident between Compound I and AmB against C. albicans, A. fumigatus and C. neoformans. Fractional inhibitory indices (FIC) were approximately 0.50 or lower, indicative of additive or synergistic activity. Results suggest that Compound I can enhance the activity of FCZ and AmB and indicate a potential role for Compound I in combination regimes against those fungi less sensitive or insensitive to Compound I when used alone.

Drug interaction and efficacy studies with Compound I combined with either AmB or FCZ against disseminated candidiasis, aspergillosis and cryptococcosis were performed. Results showed no adverse effects with combinations at high, use or lower concentrations and no antagonism of efficacy with either AmB or FCZ combined with Compound I. Against C. albicans, Compound I doses of 0.03 mg/kg and lower plus 0.03 mg/kg and lower of AmB appeared more efficacious than either agent administered alone. With FCZ similar results were found at doses of 0.31 mg/kg and lower of FCZ when combined with 0.03 mg/kg of Compound I. Against A. fumigatus, significant improvements in efficacy (10 to >800-fold in ED values) with combinations were noted with Compound I titrated between 0.03 and 2 mg/kg and with AmB between 0.03 and 0.5 mg/kg. Significant improvement in survival was seen with Compound I at 0.008 mg/kg combined with AmB at 0.12 mg/kg over the compounds administered alone.

As found in drug combination studies in vitro with Compound I and AmB, FIC values were approximately 0.50, suggesting additive or synergistic activity in vivo. Additionally, no antagonism of efficacy with FCZ in combination with Compound I was seen in studies against cryptococcosis in mice. Beneficial effects on efficacy were observed against C. neoformans with combinations of Compound I and FCZ at certain concentrations.

Given the above disclosure, it is thought that variations will occur to those skilled in the art. For example, it is thought that combination therapy using azoles other than fluconazole and pneumocandin derivatives other than Compound I may also be effective against fungal infections caused by the fungal pathogens noted. Accordingly, it is intended that the above examples should be construed as illustrative and that the invention disclosed herein should be limited only by the following claims.

What is claimed is:

[1. A method of treating fungal infection which comprises administering therapeutically effective amounts of a pneumocandin derivative with a compound selected from an azole, polyene, purine nucleotide inhibitor, pyrimidine nucleotide inhibitor, mannan inhibitor, protein elongation factor inhibitor or bactericidal/permeability increasing protein product.]

[2. The method of claim 1 which comprises administering therapeutically effective amounts of a pneumocandin derivative and a polyene.]

[3. The method of claim 1 which comprises administering therapeutically effective amounts of a pneumocandin derivative and an azole.]

4. [The] *A* method of [claim 1 wherein the pneumocandin derivative is] *treating fungal infection which comprises administering therapeutically effective amounts of*

(I)

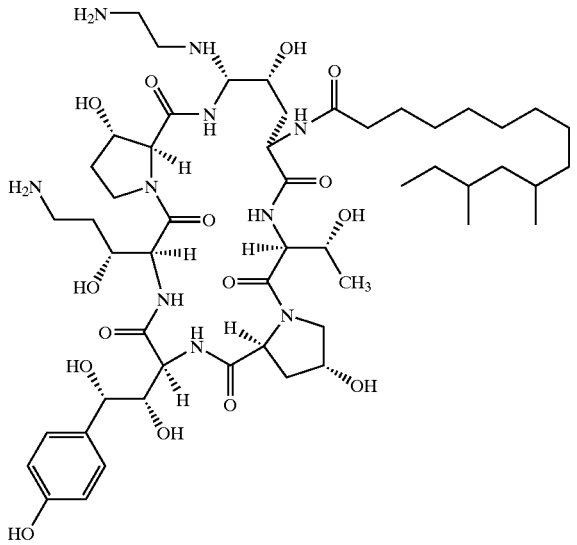

or a pharmaceutically acceptable salt thereof, *with a compound selected from an azole, polyene, purine nucleotide inhibitor, pyrimidine nucleotide inhibitor, mannan inhibitor, protein elongation factor inhibitor or bactericidal/permeability increasing protein product.*

5. The method of claim [2] *4* wherein the [pneumocandin derivative is (I)

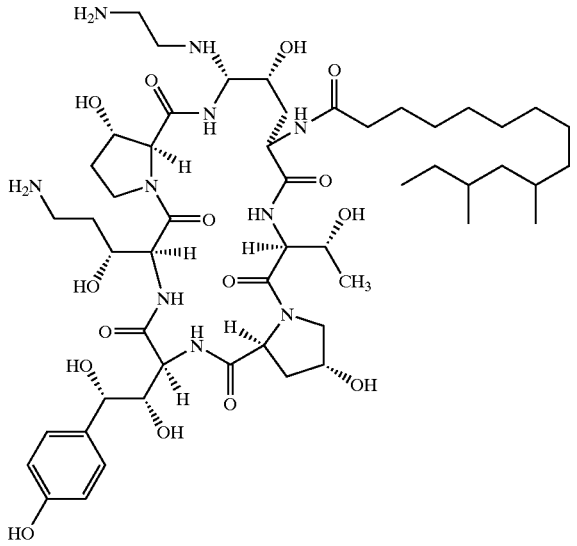

or apharmaceutically acceptable salt thereof] *compound is a polyene.*

6. The method of claim [3] *4* wherein the [pneumocandin derivative is (I)

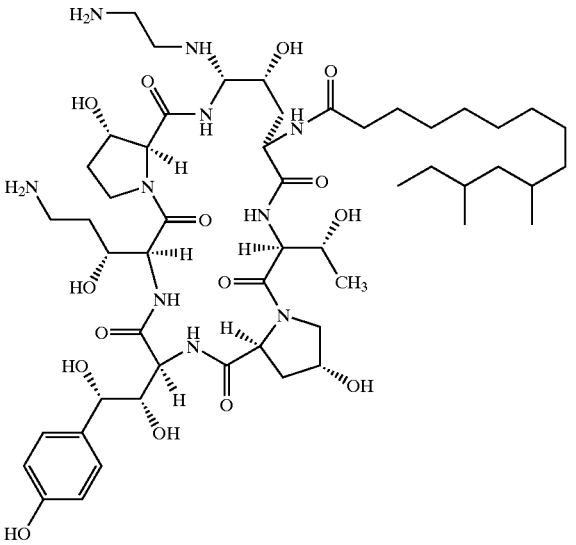

or a pharmaceutically acceptable salt thereof] *compound is an azole.*

7. The method of claim [1] *4* wherein the azole is selected from the group consisting of fluconazole, voriconazole, itraconazole, ketoconazole, miconazole, ER 30346, SCH 56592; the polyenes is selected from the group consisting of amphotericin B, nystatin or liposomal and lipid forms thereof; the purine or pyrimidine nucleotide inhibitors is flucytosine; the polyoxin is nikkomycin Z, the elongation factor inhibitor is sordarin and analogs thereof and the mannan inhibitor is predamycin.

8. The method of claim 7 wherein the azole is fluconazole.

9. The method of claim 7 wherein the polyene is amphotericin B.

10. The method of claim [1] *4* wherein the infection is caused by a fungal pathogen selected from Cryptococcus spp., Candida spp., Aspeigillus spp., Histoplasma spp., Coccidioides spp., Paracoccidioides spp. Blastomyces spp., Fusarium spp., Sporothrix spp., Trichosporon spp., Rhizopus spp., Pseudallescheria spp. dermatophytes, Paeciliomyces spp., Alternaria spp., Curvularia spp., Exophiala spp., Wangiella spp., Penicillium spp., Saccharomyces spp., Dematiaceous fungi or Pneumnocystis carinii.

11. The method of claim [2] *5* wherein the infection is caused by the fungal pathogen selected from Cryptococcus spp., Candida spp., Aspergillus spp., Histoplasma spp., Coccidioides spp., Paracoccidioides spp. Blastomyces spp., Fusarium spp., Sporothrix spp., Trichosporon spp., Rhizopus spp., Pseudallescheria spp., dermatophytes, Paeciliomyces spp., Alternaria spp., Curvularia spp., Exophiala spp., Wangiella spp., Penicillium spp., Saccharomyces spp., Dematiaceous fungi or Pneumocystis carinii.

12. The method of claim [3] *6* wherein the infection is caused by the fungal pathogen selected from Cryptococcus spp., Candida spp., Aspergillus spp., Histoplasma spp., Coccidioides spp., Paracoccidioides spp. Blastomyces spp., Fusarium spp., Sporothrix spp., Trichosporon spp., Rhizopus spp., Pseudallescheria spp., dermatophytes, Paeciliomyces spp., Alternaria spp., Curvularia spp., Exophiala spp., Wangiella spp., Penicillium spp., Saccharomyces spp., Dematiaceous fungi or Pneumocystis carinii.

13. The method of claim 10 wherein the fungal pathogen is selected from Cryptococcus spp., Candida spp. or Aspergillus spp.

14. The method of claim 11 wherein the fungal pathogen is selected from Cryptococcus spp., Candida spp. or Aspergillus spp.

15. The method of claim 12 wherein the fungal pathogen is selected from Cryptococcus spp., Candida spp. or Aspergillus spp.

* * * * *